United States Patent [19]
Anderson et al.

[11] Patent Number: 5,957,835
[45] Date of Patent: Sep. 28, 1999

[54] APPARATUS AND METHOD FOR CARDIAC STABILIZATION AND ARTERIAL OCCLUSION

[75] Inventors: Scott C. Anderson, Sunnyvale; Joseph J. Nemeth, Los Altos; Lawrence J. Voss, San Jose, all of Calif.

[73] Assignee: Guidant Corporation, Indianapolis, Ind.

[21] Appl. No.: 08/857,428

[22] Filed: May 16, 1997

[51] Int. Cl.⁶ .................................................. A61B 17/02
[52] U.S. Cl. .......................... 600/201; 600/202; 600/206; 600/219
[58] Field of Search ................................. 600/206, 215, 600/202, 219; 606/151; 128/898

[56] References Cited

U.S. PATENT DOCUMENTS

| | | |
|---|---|---|
| 4,457,300 | 7/1984 | Budde . |
| 4,637,377 | 1/1987 | Loop . |
| 5,231,974 | 8/1993 | Giglio et al. ............................ 606/206 |
| 5,339,801 | 8/1994 | Poloyko et al. . |
| 5,452,733 | 9/1995 | Sterman et al. . |
| 5,613,937 | 3/1997 | Garrison et al. . |
| 5,727,569 | 3/1998 | Benetti et al. ............................ 128/898 |
| 5,730,757 | 3/1998 | Benetti et al. ............................ 606/198 |

FOREIGN PATENT DOCUMENTS

| | | |
|---|---|---|
| 0 791 330 | 8/1997 | European Pat. Off. . |
| 0 820 721 | 1/1998 | European Pat. Off. . |
| WO 95/17127 | 6/1995 | WIPO . |
| WO 96/32882 | 10/1996 | WIPO . |
| WO 97/40738 | 11/1997 | WIPO . |

OTHER PUBLICATIONS

Harlan, Bradley J., M.D., et al., *Preparation for Cardiopulmonary Bypass, Manual of Cardiac Surgery*, Second Edition, pp. 23–32 (1994).
Harlan, Bradley J., M.D., et al., *Coronary Artery Surgery, Manual of Cardiac Surgery*, Second Edition, pp. 84–131 (1994).
The Mediflex® Vernick Positractor™ Brochure (undated).
Codman Self–Retaining, Sternal (Cardio–Vascular/Thoracic) Brochure (undated).
Codman Cardio Vasive™ Retractor System (Catalog No. 8008–109) Brochure (undated).

*Primary Examiner*—Gary Jackson
*Attorney, Agent, or Firm*—Fulwider Patton Lee & Utecht, LLP

[57] ABSTRACT

An apparatus and method of use is provided for locally stabilizing an anastomotic site during a beating heart surgical procedure which includes occluding a section of the artery receiving the bypass graft vessel. An apparatus is provided to stabilize the epicardium and the operational field, and includes a platform that can be compressed onto the epicardium or tensioned by pulling the epicardium upwardly, thereby providing a stabilized operational field. At least one occluding member provides means to occlude the section of artery receiving the bypass graft vessel. An adjustable stabilizing arm can be used in conjunction with the platform to further provide stability to the epicardium during the beating heart bypass graft procedure.

67 Claims, 8 Drawing Sheets

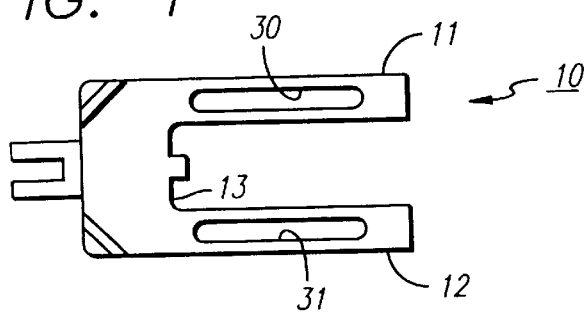
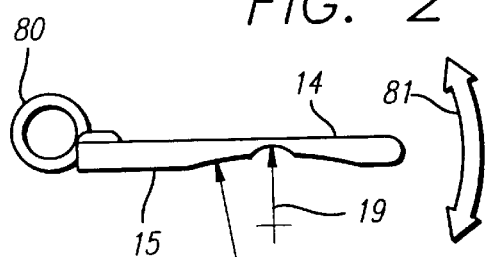
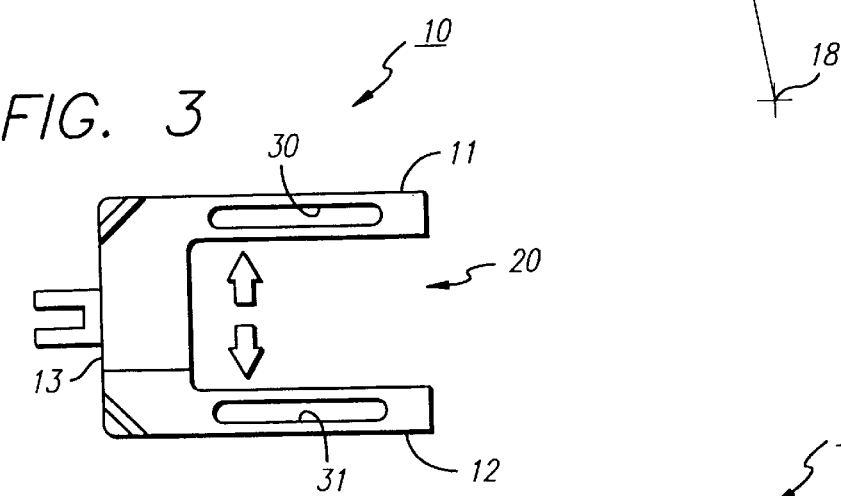
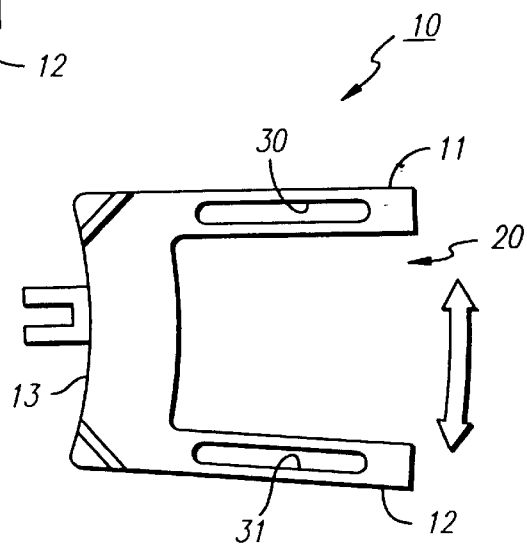

APPARATUS AND METHOD FOR CARDIAC STABILIZATION AND ARTERIAL OCCLUSION

BACKGROUND OF THE INVENTION

The invention relates generally to a system and method of stabilizing a patient's beating heart during a medical procedure, such as coronary artery bypass grafting (CABG). More specifically, the invention relates to an apparatus and method for stabilizing the epicardium and occluding the section of the artery to receive a graft vessel.

In a typical CABG procedure on a stopped heart, the patient undergoes a median sternotomy to provide access to the heart area and is put on cardiopulmonary bypass equipment (CPB) to oxygenate the blood and allow the heart to be stopped. These procedures are well known, are safe and are widely accepted for a wide range of medical procedures performed on the heart. A more thorough discussion of a typical CABG procedure can be found in Manual of Cardiac Surgery, Second Edition, by Bradley J. Harlan, MD, Albert Starr, MD and Fredric M. Harwin, BFA, MS, 1995, and a discussion of open heart procedures can be found in Textbook of Interventional Cardiology, Eric J. Topol, 1990, chapters 43–44, pages 831–867, incorporated herein by reference.

It should be understood that while the foregoing CABG procedures are generally regarded as safe and widely accepted, they are not without risks. As is known, when the patient is put on cardiopulmonary bypass equipment, the blood is continuously pumped extracorporeally where it is oxygenated and then returned to the body. Any time the blood is removed from the body there is the risk of infection such as sepsis or other infections that can be serious if not detected and treated. During the oxygenation process, micro-emboli are introduced that are believed to be a major cause of neurological damage which can be temporary or permanent. While the heart and lungs are being bypassed, the heart is infused with cardioplegic fluid to stop the heart from beating and limit damage to the muscle cells due to lack of blood. However, the lungs are not perfused with blood for many hours and this can cause many problems. Also, there is a need to prime the CPB pump with about one liter of fluid. This fluid is pumped into the patient's body in the first few seconds of CPB resulting in a hemodilution of about 20%. As the blood is transported through many feet of tubing and various oxygenators, heat exchangers, and pumps, it is in contact with foreign materials. This contact induces compliment activation which can lead to pulmonary dysfunction, renal dysfunction and further embolic complications. Further, the equipment needed to perform cardiopulmonary bypass is expensive and requires specialized medical personnel to operate and monitor.

During coronary artery bypass procedures using the beating heart approach, the region of the heart which receives the graft vessel must be stabilized so that the graft and suturing procedure can be performed on a substantially stationary epicardium. Presently, this is often performed by threading two sutures through the myocardium with curved needles, on either side of the recipient coronary artery at the site of the anastomosis. The sutures are tensioned to lift the heart and to hold the coronary artery stationary. Suture threads with curved needles swaged on one end are available for this use. Also, suture threads may be used to loop around and tighten the section of artery to be grafted, thereby occluding the artery during the procedure. Again, with the heart beating, placing these suture loops around the artery is difficult due to the movement of the heart and the epicardium surrounding the artery.

Placement of the suture loops may be somewhat difficult, as the heart is beating. The tip of the needle must be placed on the heart, and rotation of the surgeon's wrists must be performed to insert the needle through the myocardium or epicardium. Unpredictable motion of the epicardial surface during needle placement may cause laceration of the heart, puncture of the wall into the ventricle, or puncture of a coronary artery. It is therefore useful to stabilize the anastomotic area during the surgical procedure. There are devices and methods that facilitate the performance of cardiac procedures such as heart valve repair and replacement, coronary artery bypass grafting, and the like, using minimally invasive techniques to eliminate the need for a gross thoracotomy. For example, U.S. Pat. No. 5,425,705 to Evard et al. discloses an apparatus and method for thoracoscopically arresting the heart and establishing cardiopulmonary bypass, thus facilitating a variety of less-invasive surgical procedures on and within the heart and great vessels of the thorax. In one embodiment, Evard provides a thoracoscopic system for arresting a patient's heart including a clamp configured for introduction into the patient's thoracic cavity through a percutaneous intercostal penetration in the patient's chest. The clamp is positionable about the patient's ascending aorta between the coronary arteries and the brachiocephalic artery. The clamp is coupled to the distal end of an elongated handle for manipulating the clamp from a location outside of the patient's thoracic cavity.

It is known to use surgical clips or clamps for the purpose of clamping vessels or manipulating tissue. Typically, such clamps have a pair of movable jaws biased by a spring into a closed position, allowing the clamp to be placed on a vessel or portion of tissue and be firmly retained thereon. Examples of such clamps can be found in U.S. Pat. No. 4,932,955 to Merz et al.; U.S. Pat. No. 4,605,990 to Wilder et al.; U.S. Pat. No. 5,074,870 to Von Zeppelin; U.S. Pat. No. 3,809,094 to Cook; U.S. Pat. No. 4,404,677 to Springer; U.S. Pat. No. 4,051,844 to Chiulli; and U.S. Pat. No. 4,988,355 to Leveen et al.

Outside of the field of cardiac surgery, U.S. Pat. No. 5,415,666 to Gourlay et al. discloses a tethered clamp retractor used for tissue manipulation. The tissue manipulation system includes a tethered clamp, a clamp applicator for positioning the clamp through a trocar sleeve and applying the clamp to a tissue location in the abdominal cavity, and a rigid positioning shaft for engaging the clamp and/or tether to manipulate the clamp.

In view of the shortcomings of the prior art devices, there is a specific need for an apparatus and method for locally stabilizing an anastomotic site during a beating heart coronary artery grafting procedure. What has been needed and heretofore not available is a method of stabilizing the beating heart during a medical procedure without having to perform CPB and subjecting the patient to the attendant risks and complications. The present invention solves the problems of the prior art methods without the resulting risks.

SUMMARY OF THE INVENTION

The present invention is directed to an apparatus and method of use for locally stabilizing an anastomotic site of a beating heart during a cardiac surgical procedure, and occluding a section of artery to receive a bypass graft. More specifically, an apparatus is provided to stabilize the epicardium in an area referred to herein as the operational field, which includes the area where a section of a coronary artery receives a bypass graft. The invention further includes means for occluding the artery during the bypass grafting procedure.

The invention includes a platform having a top surface and a bottom surface, with at least a portion of the bottom surface configured for contacting the epicardium of the heart. A pair of occluding members are configured for slidable and vertical movement within the platform for positioning over and occluding a section of artery. The platform can be sutured or otherwise attached to the epicardium thereby defining an operation field within the platform on the epicardium, and stabilizing the epicardium within the operational field. By temporarily attaching the platform to the epicardium, a slight tensioning or stretching of the epicardium occurs which results in a stabilizing effect around the platform. The occluding members are positioned over and into contact with the epicardium surface over the artery, and temporarily locked in place thereby temporarily occluding a section of artery in the operational field.

In one embodiment, the platform has a substantially U-shaped configuration for defining the operational field. The platform includes a pair of legs connected by a connecting member, with the legs each having a slot in which the occluding member is retained for slidable movement. The connecting member can be adjustable so that the distance between the legs can be adjusted, thereby adjusting the size of the operational field that is stabilized during the grafting procedure. Alternatively, the connecting member can be malleable thereby permitting the legs to be pivoted, thereby adjusting the distance and angle between the legs so that they can be more easily positioned over the artery to be occluded.

One advantage of the present invention is to provide occluding members that are slidably adjustable within the slots of the legs in the platform. The occluding members can be adjusted so that they can be positioned over the section of artery to be grafted and then temporarily locked in place by twisting the members into locking engagement with the slots.

In one embodiment, to assist in further stabilizing the operational field, an adjustable arm having a first end for removable attachment to the top surface of the platform is provided. The adjustable arm has a second end for removable attachment to a support that is stationary relative to the platform. Typically, the stationary support can include a rib retractor on which the second end of the adjustable arm is clamped.

In the preferred method of stabilizing the epicardium and occluding the section of artery to be grafted, the platform is positioned over the artery to be grafted. The platform can be sutured in place or attached by other means, generally if the adjustable arm is not attached. Once the platform is attached to the epicardium, the area becomes stabilized so that the occluding members can be positioned over the artery and locked into engagement in the slots, thereby occluding the artery. The medical procedure is then performed, wherein a vessel is grafted in an end-to-side grafting procedure which is known in the art. After the medical procedure is performed, the platform is removed from the epicardium.

In an alternative method, the platform with the adjustable arm attached is positioned on the epicardium and the second end of the adjustable arm is temporarily attached to the stationary support. The adjustable arm, since it is flexible, can be used to position the platform and slightly compress the platform onto the epicardium, whereby the adjustable arm is then locked so that it is rigid. In the locked position, the adjustable arm is substantially rigid and applies slight compressive force to the platform, thereby stabilizing the epicardium. Alternatively, the adjustable arm can be used to pull the platform, which is attached to the epicardium, upwardly thereby tensioning and stabilizing the operational field. Thereafter, the occluding members are positioned over the artery and locked into place in the slots in order to occlude the artery during the grafting procedure. After the grafting procedure is completed, the adjustable arm is unlocked, thereby returning the arm to flexibility, and the device is removed from the patient.

Other features and advantages of the invention will become apparent from the following detailed description, taken in conjunction with the accompanying drawings which illustrate, by way of example, the features of the invention.

BRIEF DESCRIPTION OF THE DRAWINGS

FIG. 1 is a top view of the platform used to stabilize the epicardium.

FIG. 2 is a side elevational view depicting the platform of FIG. 1 used to stabilize the epicardium.

FIG. 3 is a top view depicting the platform wherein the connecting member for the legs is adjustable.

FIG. 4 is a top view of the platform wherein the connecting member is malleable so that the legs can be adjusted.

DETAILED DESCRIPTION OF THE PREFERRED EMBODIMENTS

Figure 5:
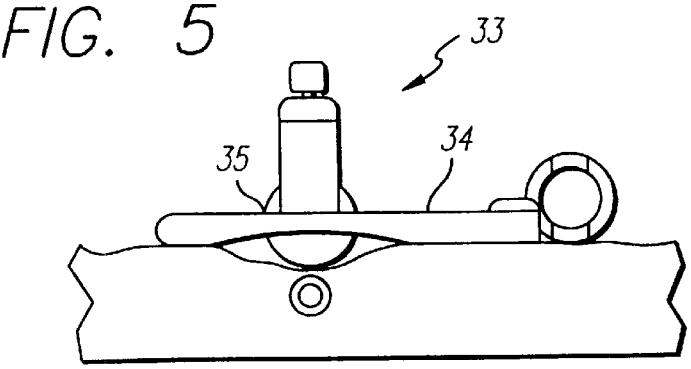
FIG. 5 is an elevational view depicting the platform wherein the occluding member is positioned over an artery.

The present invention provides an apparatus and method for use for stabilizing the epicardium of a beating heart during a cardiac surgical procedure, such as bypass grafting, and to occlude a section of artery receiving the bypass graft vessel. The apparatus of the invention stabilizes the epicardium in the operational field, which includes the area where a section of a coronary artery receives a bypass graft vessel. The invention further includes the apparatus and method for occluding a section of the artery where the bypass graft procedure occurs.

In keeping with the invention, as shown in FIGS. 1–4, platform 10 has a U-shaped configuration which includes first leg 11 and second leg 12 in substantially parallel relationship and spaced apart. The first and second legs are connected by connecting member 13 which, in FIGS. 1 and 2, is a rigid member which maintains the first and second legs in a parallel relationship. Platform 10 also includes top surface 14 and bottom surface 15, where at least a portion of the bottom surface is configured for contact with the epicardium of the heart.

As depicted in FIG. 2, bottom surface 15 of the platform is concave. First concave portion 18 is provided so that when the bottom surface of the platform is pressed onto the epicardium or attached to the epicardium, in the area of a coronary artery, the concave portion is positioned over the coronary artery so that it does not inadvertently occlude the artery. As will be described herein, means are provided to intentionally occlude a section of the artery, however, it is not intended that the platform itself, and importantly the bottom surface inadvertently occlude a portion of artery during the medical procedure. The radius of concave portion 18 can vary depending upon the application, and may range from approximately 3 inches to about 12 inches. Preferably, the radius of concave portion 18 is approximately 8 inches. It also may be desirable to provide second concave portion 19 that has a smaller radius than the first concave portion. The second concave portion can then be positioned over the artery without occluding it. The second concave portion 19 has a radius in the range of about 0.5 to 3.0 inches and preferably is about 1.3 inches.

The area encompassed by the boundaries of first leg 11, second leg 12 and connecting member 13 define operational field 20. If it is desired to provide a larger or smaller operational field, the dimensions of platform 10, and specifically the distance between first leg 11 and second leg 12 can be varied to suit the particular application. In order to provide flexibility for the surgeon performing the bypass procedure, it may be desirable to vary the size of the operational field 20 during the procedure. Depicted in FIGS. 3 and 4, the distance and angle between first leg 11 and second leg 12 is adjustable. In FIG. 3, connecting member 13 can be a two-piece member, one slidable within the other in a telescoping manner, so that the distance between the first leg and the second leg can be varied, while the legs remain parallel to each other. The platform depicted in FIGS. 1–3 can be formed of a rigid material including metal alloys, stainless steel, polycarbonate, Ultem® (Ultem® is available from General Electric Plastics, Pitsfield, Mass.) or rigid polymers. Importantly, the materials must be biocompatible, and preferably sterilizable, however, the platform is configured and designed for single use applications and would not require further sterilization after a single procedure.

Referring to an alternative embodiment of platform 10, as shown in FIG. 4, connecting member 13 is formed from a malleable material, which provides flexibility so that first leg 11 and second leg 12 can be essentially pivoted apart to increase or decrease the size of operational field 20. Examples of malleable materials include a malleable wire made from 304 stainless steel wire covered with a polymer, such as polyethylene, urethane, and silicone.

Since the function and purpose of platform 10 is to provide stabilization of the epicardium in the operational field, it is intended that it be used either alone, or in conjunction with further apparatus as will be described herein. When used alone, it may be desirable to temporarily attach platform 10 to the epicardium. In that regard, as depicted in FIGS. 1–4, a plurality of grooves 21 are provided on top surface 14. The grooves are indentations for receiving a suture thread that is passed through the epicardium with a needle or other means, and positioned in the groove and tightened so that the platform can be sutured to the epicardium. In the specific embodiments depicted in the drawings, there are four grooves 21 for receiving sutures only two of which are shown in the figures, thereby providing four attachment points on platform 10. At least three attachment points are preferred, and more attachment points may be desired. With at least three attachment points between platform 10 and the epicardium, operational field 20 can be placed in tension, which provides stabilization. More or less grooves 21 can be provided, and it is contemplated that other attachment means can be substituted for the grooves, including apertures passing through platform 10, tabs attached to the sides or top of the platform, and similar attachment means. In addition, in some circumstances suture threads may not be ideal and it may be desirable to use other attachment means such as hooks, screws or helical fasteners. For example, hooks on the sides of platform 10 or on bottom surface 15 may be used as attachment points. Further, helical screws such as the Origin Tacker®, manufactured and sold by Origin MedSystems, Menlo Park, Calif., can be used to attach platform 10 to the epicardium. The attachment means is biocompatible and in the case of suture threads, helical screws, and similar attachment means, they are bioabsorbable and will be absorbed into the body over a short period of time.

While dimensions may vary depending upon a particular application, in a preferred embodiment the distance between first leg and second leg is in the range of approximately 0.2 to 2.0 inches. The length of legs 11,12 also will vary depending upon the application, and preferably are in the range of about 0.5 to 3.5 inches. In the embodiments depicted in FIGS. 3 and 4, the distances between the legs can be varied by the surgeon at the time of the procedure.

The platform may be adapted to include means for occluding a section of the artery to be grafted so that the platform provides not only a stabilization function, but an occluding function during the bypass procedure. As depicted in FIGS. 1, 3–7, 16–17, and 21–23, the platform includes a pair of slots and movable occluding members for occluding the artery.

In a preferred embodiment, platform 10 includes first slot 30 and second slot 31 in first leg 11 and second leg 12 respectively. The slots are configured for receiving first occluding member 32 in first slot 30 and second occluding member 33 in second slot 31. The occluding members 32,33 are configured for slidable movement within the slot and vertical movement into and out of engagement with either the artery, or the epicardium directly above the artery so that the first and second occluding members can occlude the artery during the bypass procedure.

First and second occluding members 32,33 are slidably retained in first slot 30 and second slot 31, respectively, so that the occluding members cannot be removed from the slot without substantial force being applied. While it is intended that the occluding members freely slide in the slot and move vertically, it is equally important that they not be inadvertently removed from the slot during the medical procedure for the protection of the patient. Thus, by design, occluding members 32,33 cannot easily be removed from slot 30,31. In an alternative embodiment, occluding members 32,33 may be tethered to platform 10 for positioning in slots 30,31 during the bypass procedure.

Figure 6:
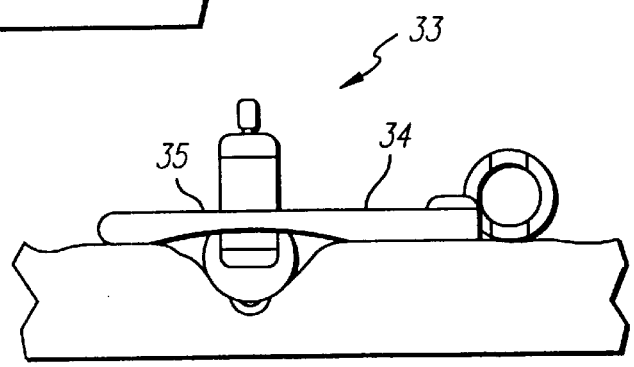
FIG. 6 is an elevational view of the platform positioned on the epicardium with the occluding member in contact with and occluding the artery.

As will be more fully described herein, as depicted in FIGS. 5 and 6, first and second occluding members 32,33 are moved from parked position 34 where they are out of the surgeon's way at the beginning of the bypass procedure, to engagement position 35, whereby the occluding members are moved into contact with the artery or the epicardium directly above the artery.

Figure 7:
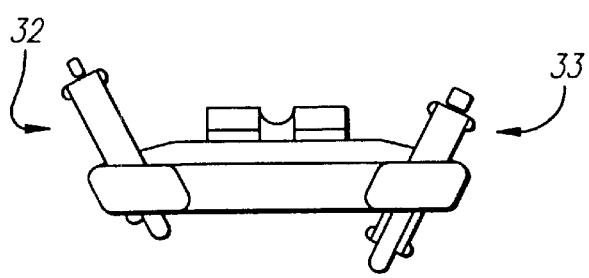
FIG. 7 is an elevational view of the platform depicting the occluding members at an angle to provide easier access to the operational field.
Figure 8:
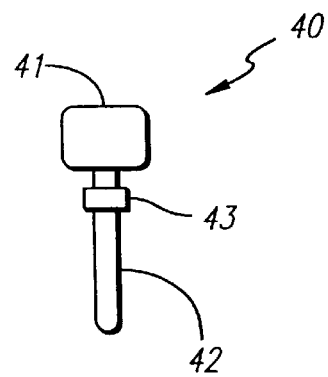
FIG. 8 is a front elevational view of the elongate body which forms part of the occluding member.
Figure 9:
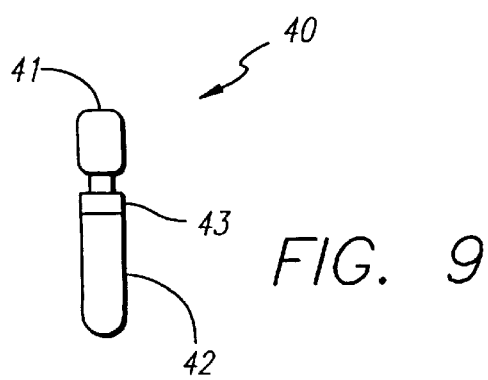
FIG. 9 is a side elevational view of the elongate body of FIG. 8 turned 90°.
Figure 10:
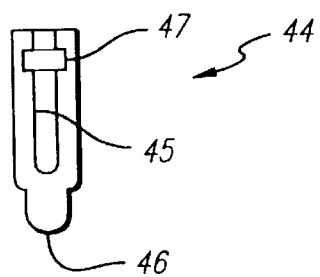
FIG. 10 is cross-sectional view depicting a body portion for receiving the elongate member thereby forming the occluding member.
Figure 17:
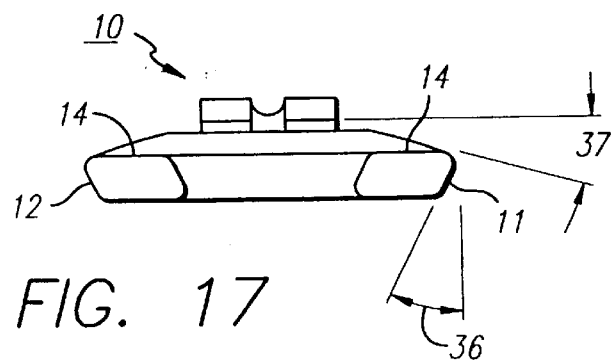
FIG. 17 is a front elevational view depicting the platform of FIG. 16, in which the angulation of the slots are more clearly depicted.
Figure 16:
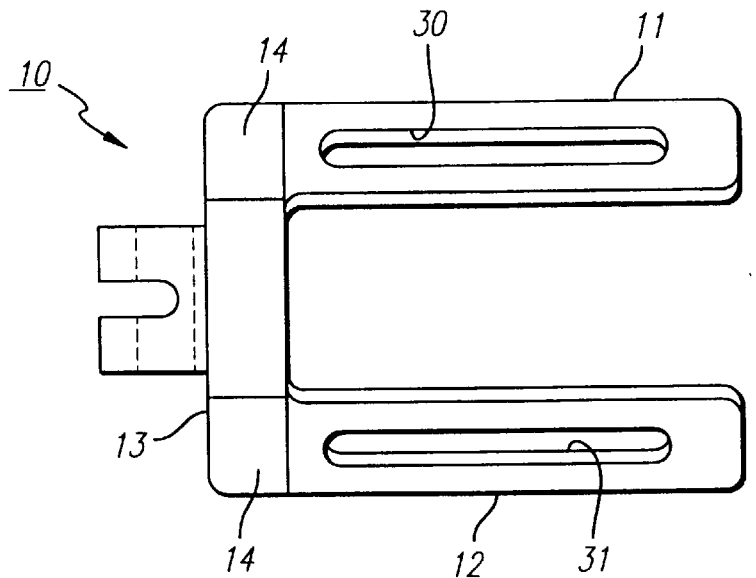
FIG. 16 is a top elevational view of the platform depicting angulated slots.

Platform 10 can be designed for use with only a single occluding member, which may be desirable under certain conditions. With two occluding members projecting upwardly from the surface of platform 10, it may reduce the ability of the surgeon to perform certain of the bypass procedures. It may be desirable to use only one occluding member to occlude the section of the artery under conditions where operating space is tight. Also, under circumstances where the artery being grafted is totally occluded, it may unnecessary to use two occluding members since the upstream portion of the artery already is occluded. In keeping with one preferred embodiment of the invention, as depicted in FIGS. 7 and 16–17, it may be desirable to angulate slots 30,31 so that occluding members 32,33 also are angulated. In this embodiment, the occluding members are angulated so that they provide easier access to the operational field, since they are more out of the way than if the slots are perpendicular in the platform. Thus, first angle 36 is provided so that occluding members 32,33 are angulated thereby exposing greater access to operational field 20. Preferably, slots 30,31 include first angle 36, measured from the vertical, in the range of about 5° to 45°, and more preferably in the range of about 20° to 30°. The top surface 14 of slots 30,31 also are angulated, as indicated by second angle 37, preferably second angle 37°, measured from the horizontal, is in the range of about 0° to 30°, and more preferably in the range of 10° to 22°.

As depicted in FIGS. 8–15, several embodiments of first and second occluding members 32,33 are depicted. The occluding members include rigid elongate core 40 having tab 41 at one end, shaft 42 extending from tab 41, and flange 43 located on the shaft. Core 40 is intended to be formed from a metal or metal alloy, such as stainless steel, or a rigid polymer material. Occluding members 32,33 also comprise body portion 44 having slot 45 for receiving shaft 42. Body portion 44 also includes occluding end 46 configured for direct engagement with the artery, or the epicardium directly above the artery. The occluding end and body portion can be formed from various materials, including silicone, urethane, polycarbonate, and polypropylene. Other similar materials also may be suitable.

Figure 12:
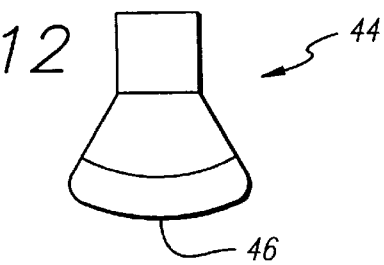
FIG. 12 is a front elevational view of the body portion depicting the occluding end which contacts the. artery.
Figure 13:
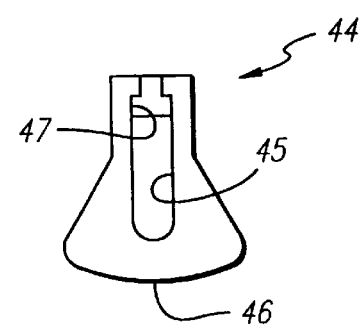
FIG. 13 is a cross-sectional view of the body portion of FIG. 12, depicting the recess for receiving the elongate body of FIGS. 8 and 9.

In one embodiment, as depicted in FIGS. 12 and 13, occluding end 46 provides an atraumatic contour so that when contacting the artery or epicardium, it does not damage or tear any portion of the artery or the epicardium.

In a preferred embodiment as depicted in FIGS. 8–13, elongate core 40 is inserted into slot 45 of body portion 44. Flange 43 locks into recess 47 in the body portion thereby providing an interference fit, making it extremely difficult to remove core 40 from portion 44.

Figure 11:
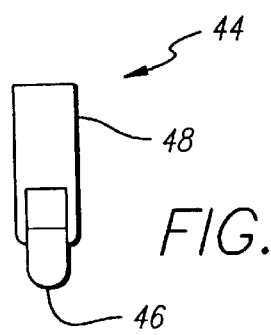
FIG. 11 is an elevational view of the body portion of FIG. 10.

As can be seen in FIG. 11, body portion 44 includes retainer 48 which is configured to substantially match the configuration of first and second slots 30,31. Thus, retainer 48 allows first and second occluding members 32,33 to slide within the slots. Preferably, shaft 42 has a rectangular configuration as does slot 45 of the body portion 44. As will be described more fully herein, first and second occluding members 32,33 must be locked in position in first and second slots 30,31. In order to lock the occluding members in position, a twisting force is applied causing an interference fit between the occluding members and the slots. In order to provide sufficient locking force, shaft 42 and slot 45 are rectangular, as opposed to circular for example, so that the necessary twisting or torquing action can be applied.

Figure 14:
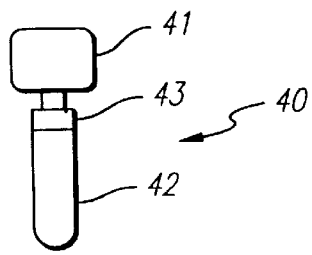
FIG. 14 is an elevational view of an alternative embodiment of the rigid elongate core.
Figure 15:
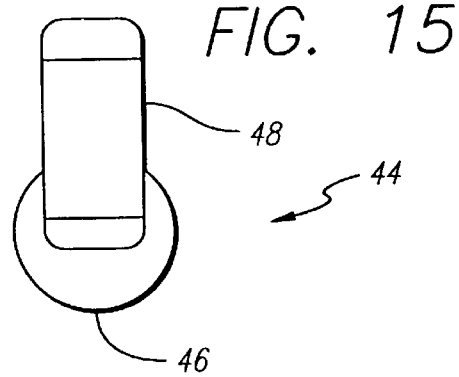
FIG. 15 is a front elevational view of an alternative embodiment depicting the body portion of the occluding member, further depicting the more circular occluding end for contacting the coronary artery.

As depicted in FIGS. 14 and 15, the preassembled occluding members 32,33, include occluding end 46 that is more circular, rather than contoured as depicted in FIGS. 12 and 13. The configuration of occluding end 46 is a matter of choice as long as it provides an atraumatic surface to occlude the artery.

Figure 18:
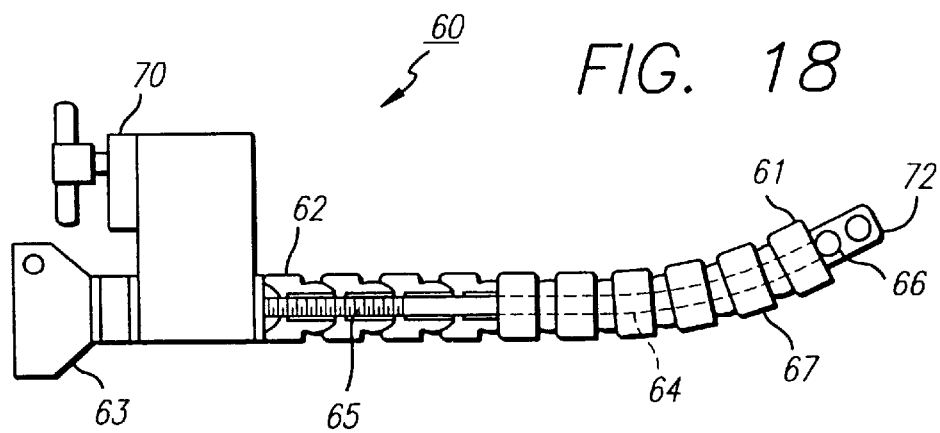
FIG. 18 is an elevational view of an adjustable arm for use in conjunction with the platform.
Figure 19:
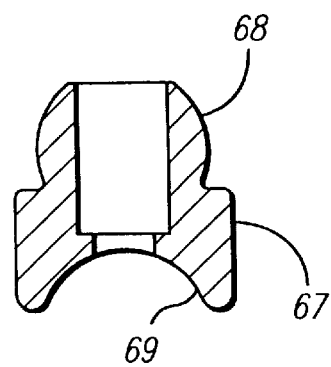
FIG. 19 is a cross-sectional view of a link associated with the adjustable arm.

The platform also can be used in conjunction with an adjustable arm for stabilizing the epicardium. As depicted in FIG. 18, adjustable arm 60 includes distal first end 61 and proximal second end 62. The adjustable arm 60 is flexible in one configuration and rigid in a second configuration. Locking member 63 is located at second end 62 and is attached to threaded cable end 65 of cable 64. A locking ball 66 is positioned at the distal end of the cable and in one position locking member 63 allows the cable to be flexible, while in a locked position the cable is tightened thereby providing a rigid adjustable arm. The adjustable arm further includes a plurality of links 67, one of which is depicted in FIG. 19.

Figure 20:
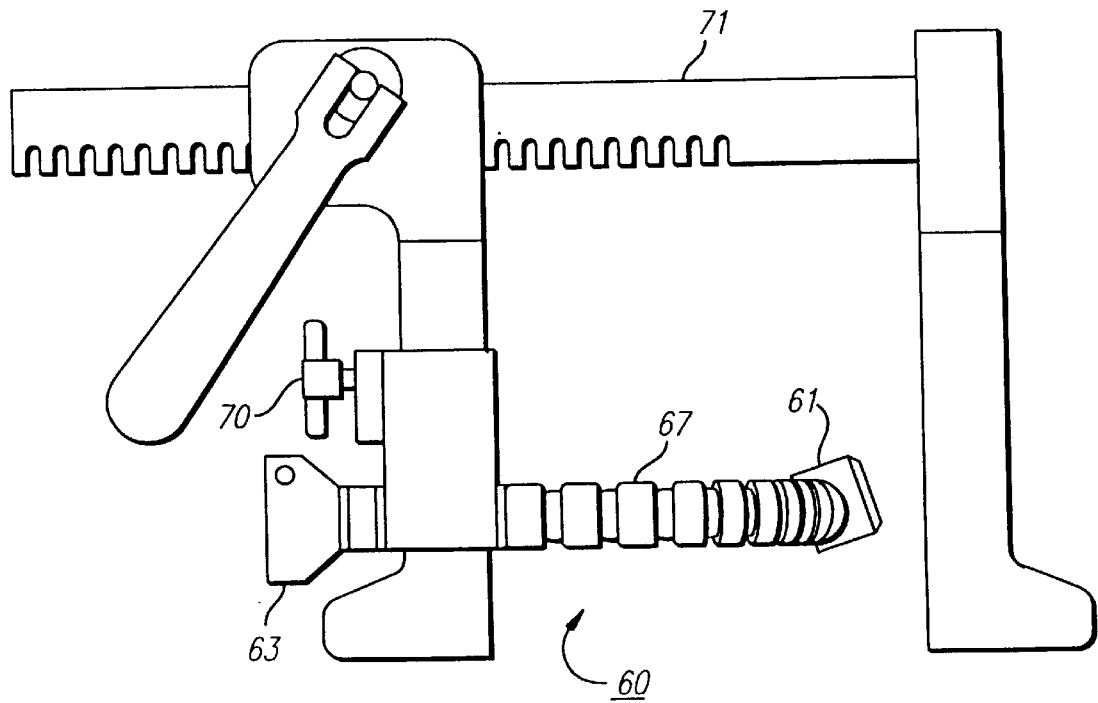
FIG. 20 is a top elevational view of the adjustable arm connected to a rib retractor.

The links include a ball portion 68 which essentially acts as a ball and socket joint with socket section 69 so that the adjustable arm is flexible in the unlocked position. As can be seen in FIG. 20, adjustable arm 60 includes proximal clamp 70 which is adapted to releasably attach to, for example, rib retractor 71 or any other similar stationary support in the operation area. At the opposite end of the adjustable arm is a distal clamp 72 used to releasably attach to platform 10.

Both adjustable arm 60 and rib retractor 71 are known in the art and commercially available. For example, an adjustable arm referred to as HUANG Universal Flexible Arm® is available from Codman and Shurtleff, Inc., Randolph, Mass. Rib retractors also are commercially available, one of which is ANKENEY Sternal Retractor, available from Codman and Shurtleff, Inc., Randolph, Mass.

Figure 21:
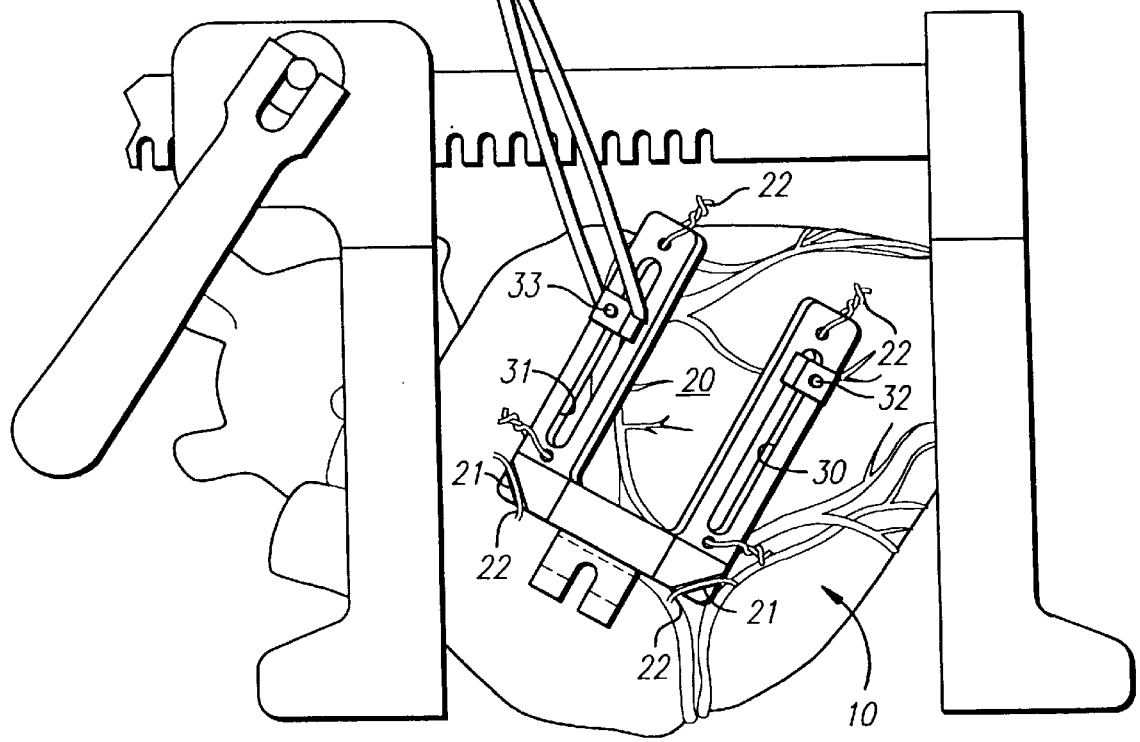
FIG. 21 is a top elevational view of the platform positioned on the epicardium of the heart and further depicting the occluding members in contact with a section of the artery to receive a bypass graft vessel.

In keeping with the preferred method of using the invention, platform 10 can be used with or without adjustable arm 60. As depicted in FIG. 21, platform 10 has been positioned on the epicardium and temporarily attached thereto by suture threads 22. Once the suture threads have been tightened to temporarily attach the platform to the epicardium, the epicardium is tensioned thereby stabilizing the operational field. At this point, the artery is not occluded since first and second concave portions 18,19 on the bottom of the platform do not press down on the artery to restrict blood flow. While it is optional to use the occluding members of the invention to occlude the artery prior to performing the bypass procedure, other occluding means are available, including known occluding means such as looping a suture thread around the artery and tightening it to occlude the artery. In the preferred method of use, at least the first occluding member 32 is moved from parked position 34 to engaged position 35 directly over the artery, and then pressed downwardly onto the artery or the epicardium directly over the artery to occlude the artery. With forceps or the surgeon's fingers, tab 41 is tightly gripped and the first occluding member is twisted approximately 90° so that it creates an interference fit within first slot 30. The occluding member now remains firmly wedged within the first slot and occludes the artery for the surgeon to begin the grafting procedure. Preferably, the same procedure is employed to wedge the second occluding member 33 in second slot 31 so that the section of artery between the first and the second legs 11,12 of the platform is completely occluded. The surgeon then performs the bypass graft procedure which is well known in the art. Thereafter, the occluding members are released by twisting each of them approximately 90° so that they are again slidably movable within the first and second slots. The suture threads are cut and the platform is then removed from the patient.

Figure 22:
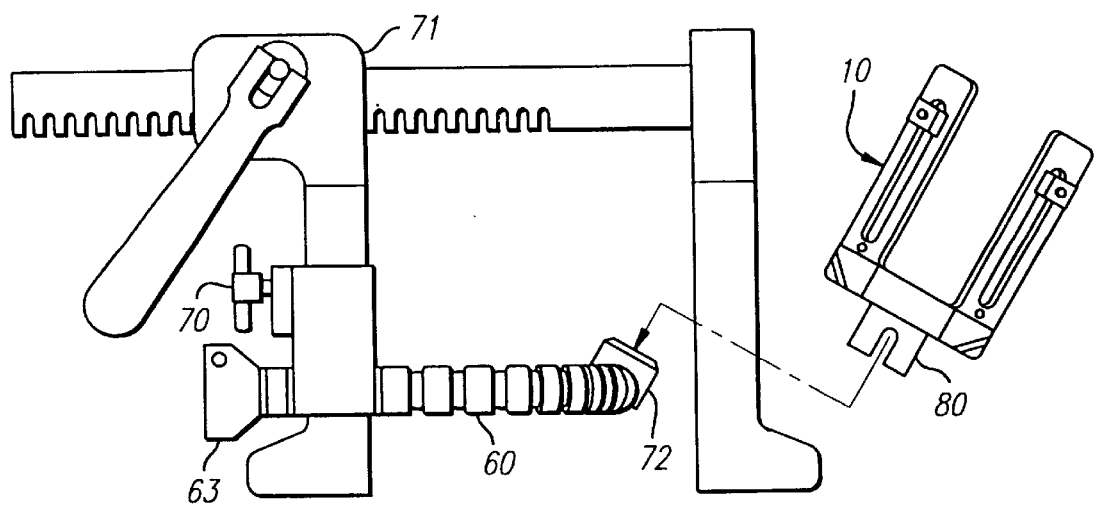
FIG. 22 is a top elevational view depicting the platform being connected to the adjustable arm.
Figure 23:
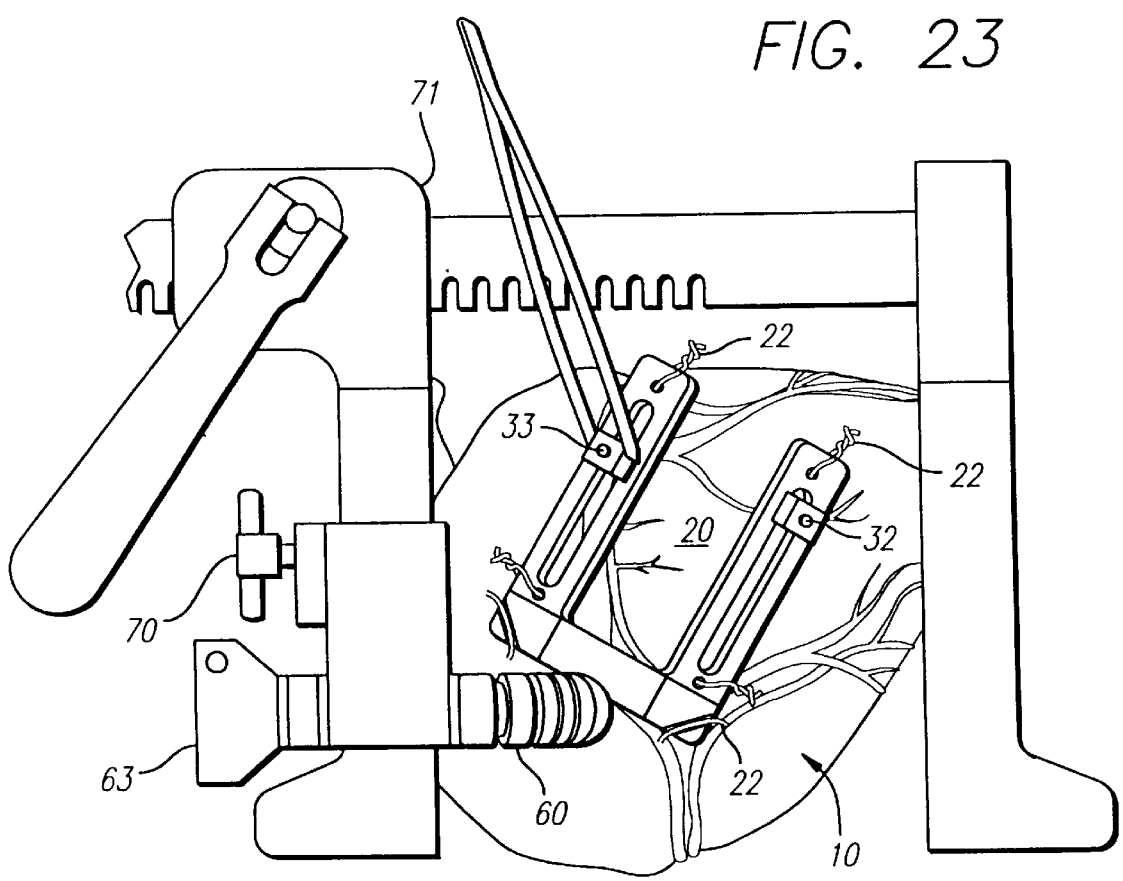
FIG. 23 is a top elevational view depicting the platform attached to the adjustable arm, further depicting the platform being positioned on the epicardium and the occluding members occluding a section of an artery.

In an alternative method of use embodiment, as depicted in FIGS. 22 and 23, platform 10 is removably attached to adjustable arm 60. Distal clamp 72 at the distal end of the adjustable arm is attached to hub 80 on platform 10. The connection between distal clamp 72 and hub 80 preferably provides for pivotal movement of the platform as can be seen, for example, in FIG. 2. While FIG. 2 does not show the attachment of distal claim 72 to hub 80, the pivoting motion is indicated by arrows 81. The ability of platform 10 to pivot is advantageous due to the contours of the heart and provides one more degree of adjustment in an operating theater that is limited for space.

With adjustable arm 60 attached to platform 10, the platform is then positioned on the epicardium and temporarily attached thereto, by the means herein described, such as by suturing, attachment hooks, helical screws, and the like. Proximal clamp 70 at the proximal end of the adjustable arm is then clamped onto rib retractor 71 or a similar stationary support. Thereafter, locking screw 63 engages threaded cable end 65 to tighten cable 64, thereby converting the flexible adjustable arm 60 to a rigid and stationary arm. Thus, platform 10 is now stationary and if compressed onto the epicardium, provides a stabilized operating field. If desired, when adjusting the adjustable arm and locking it into engagement so that it becomes rigid, it can be pulled upwardly away from the beating heart thereby placing the operational field in slight tension, as opposed to compression. In either direction, i.e., tensioning or compressing the platform onto the epicardium, will result in stabilizing the operational field. Thus, the surgeon has the option of tensioning or compressing the epicardium, depending upon the particular application to benefit the patient.

With continued reference to FIGS. 22 and 23, the preferred method includes attaching the adjustable arm to the platform and temporarily suturing the platform to the epicardium. Once the adjustable arm is locked and becomes rigid, one or both of first and second occluding members 32,33 can be locked into position in the slots to occlude the section of artery. The surgeon then completes the bypass procedure, unlocks the occluding members, removes the sutures from the platform, then removes the adjustable arm and platform from the patient.

In those circumstances where an adjustable platform is used, such as those depicted in FIGS. 3 and 4, it provides an added degree of adjustability in positioning the platform so that the occluding members can be moved into position over the artery. Thus, as depicted in FIG. 4, when positioning the platform, first leg 11 can be moved away from or closer to second leg 12 so that the occluding members can be more accurately positioned over the artery.

Figure 24:
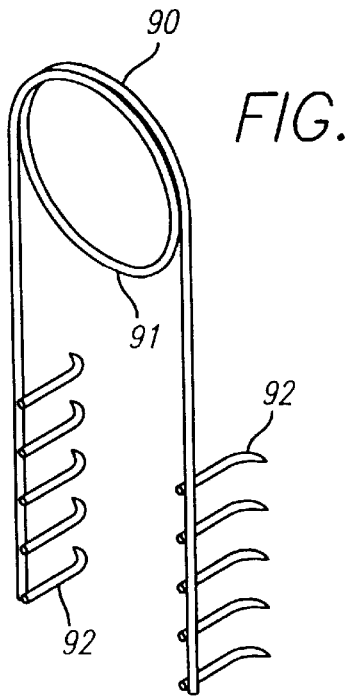
FIG. 24 is an elevational view of a wire retractor for use with the platform stabilizing invention.
Figure 25:
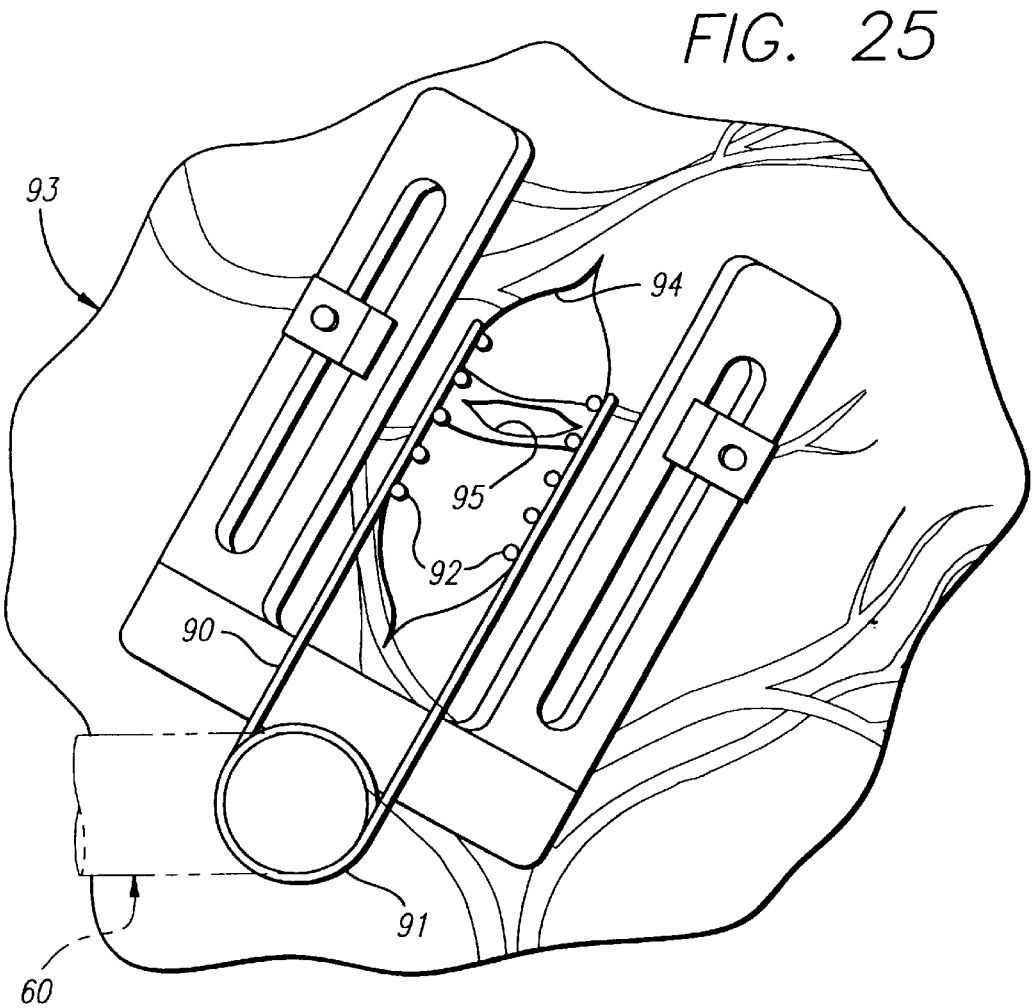
FIG. 25 is a perspective view of the platform positioned on the epicardium depicting the retractor of FIG. 24 used to pull back the epicardium to expose the arteriotomy site.
Figure 26:
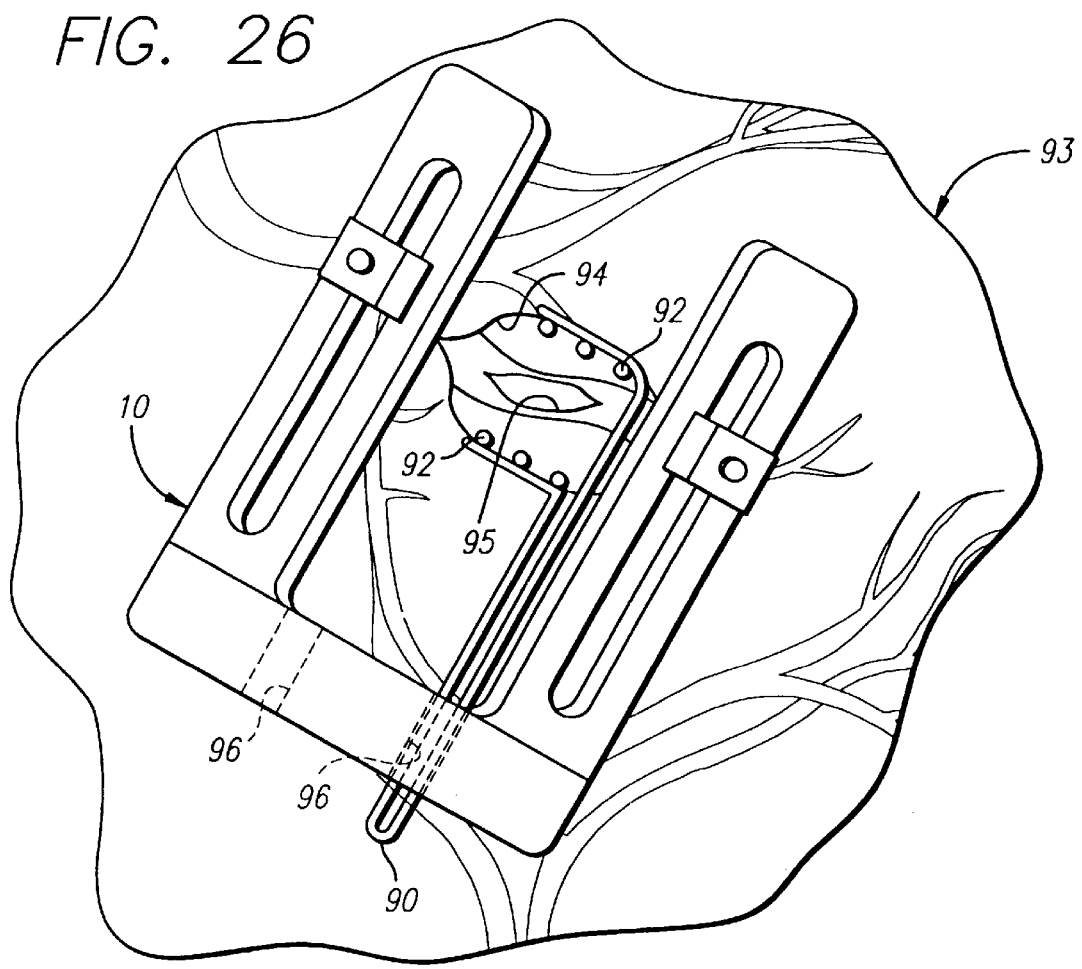
FIG. 26 is a perspective view of the platform positioned on the epicardium, depicting the retractor of FIG. 24 positioned through a slot in the platform and holding back the epicardium to expose the arteriotomy site.

In an alternative embodiment of the invention, as depicted in FIGS. 24–26, means are provided to further stabilize the epicardium and hold open the arteriotomy site to better expose the arteriotomy. In that regard, retractor 90 having loop 91 is provided as a stainless steel wire (or nickel-titanium/Nitinol), further having hooks positioned at the distal ends of the wire. As depicted in FIG. 25, loop 91 is positioned around adjustable arm 60 (only partially shown for clarity) with hooks 92 embedded in the heart muscle 93 or epicardium. The arteriotomy site 94 is thus fully opened and stabilized for the surgeon to perform arteriotomy 95 on the artery. Wire 90 can be shaped or fashioned into virtually any configuration so that it functions to allow hooks 92 to penetrate the heart muscle and provide a fully exposed and stabile arteriotomy site. Alternatively, as shown in FIG. 26, retractor 90 can be bent to slide through slot 96 in the platform and further bent so that hooks 92 hold open the arteriotomy site in the manner depicted. Retractors similar to those depicted in FIGS. 24–26 are commercially available, for example, in plastic surgery applications, and are sold under various tradenames including Parsonnet Retractor, available from Pilling Weck, Inc., Research Triangle Park, N.C.

Other embodiments of retractors for use with the present invention to hold back the epicardium can include a pair of jaws attached to wire 90, similar to a clothespin, which would attach to the epicardium. Also, retractor 90 can be advanced and retracted into position by a ratcheting means, such as a rack and pinion or a zip tie. A rack and pinion means can include ratcheting to tension retractor 90, but which requires a one-eighth or one-quarter turn to release the tension on retractor 90. Further, loop 91 can provide a tension force to hooks 92 if it is formed from, for example, stainless steel that has a resiliency or a tensioning loop 91.

Portions of retractor 90 might be annealed so that it is more maneuverable, yet still retaining the tensioning properties.

Figure 28:
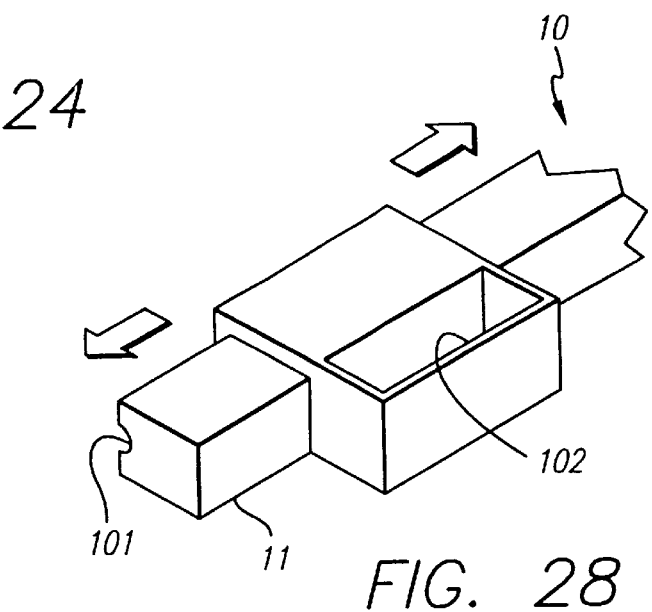
FIG. 28 is a partial view of one leg of the platform, in perspective, depicting a carriage for slidable movement along the leg.
Figure 27:
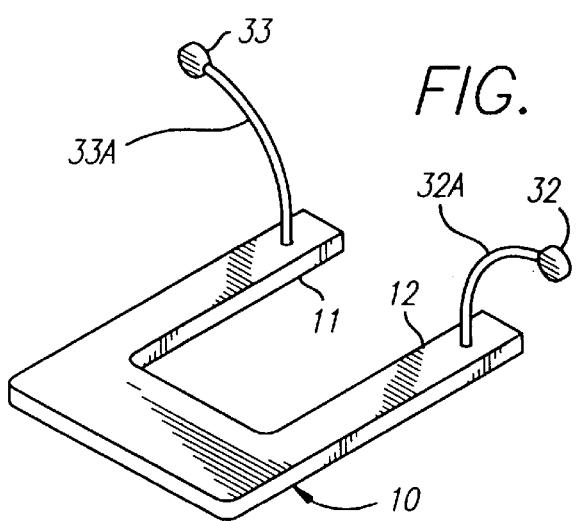
FIG. 27 is a perspective view of the platform further depicting an alternative embodiment of the occluding members for occluding the artery.
Figure 29:
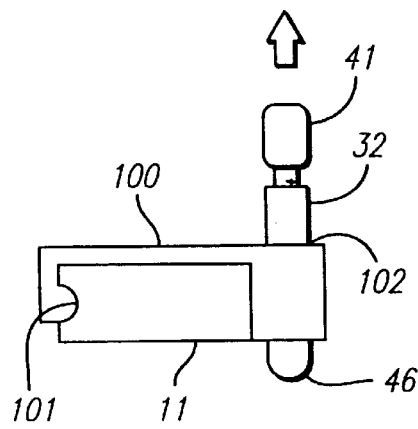
FIG. 29 is an end elevational view, partially in cross-section, of the leg and carriage assembly of FIG. 28, with the occluding member retained in the carriage member.

In a further alternative embodiment, as depicted in FIGS. 27–29, alternative means for occluding the artery are provided. Referring to FIGS. 27, occluding members 32,33 are attached to legs 11,12 of platform 10. The occluding members include positioning arms 32A,33A, which are configured so that the occluding members can easily be positioned over an artery or the epicardium just above the artery. Thus, positioning arms 32A,33A are formed from a malleable wire, or similar material, so that they can be bent in order to more easily position occluding members 32,33. The positioning arms should be stiff enough so that as the occluding members are compressed onto the artery or the epicardium above the artery, they will remain in place by occluding the artery until moved by the surgeon.

Similarly, an alternative means for occluding the artery is depicted in FIGS. 28–29, in which a portion of platform 10 is depicted, with leg 11 providing support for movable carriage 100. The movable carriage slides over leg 11 and is retained thereon by sliding along carriage slot 101. The movable carriage includes an occluding member retainer 102, which is configured for receiving first and second occluding members 32,33, as herein described. As depicted in FIG. 29, occluding member 32 is configured for vertical movement within retainer 102. In use, carriage 100 is used to position occluding member 32 over an artery or the epicardium directly above the artery. Thereafter, occluding member 32 is pressed into contact with the artery or epicardium above the artery, and tab 41 is then twisted 90° by the surgeon's fingers or using forceps so that the occluding member is temporarily locked or wedged in retainer 102. After the bypass procedure is completed, tab 41 is then twisted 90° thereby releasing occluding member 32 from occluding the artery.

While a particular form and use of the invention has been illustrated and described, and particular dimensions and materials of manufacture have been disclosed, it will also be apparent to those skilled in the art that various modifications can be made without departing form the spirit and scope of the invention. Accordingly, it is not intended that the invention be limited except by the appended claims.

What is claimed is:

1. An assembly for stabilizing the epicardium of the heart and occluding a section of an artery, comprising:
    a platform having a top surface and a bottom surface, at least a portion of the bottom surface configured for contacting the epicardium of the heart;
    at least one occluding member configured for adjustable movement relative to the longitudinal axis of the platform;
    means for removeably attaching the platform to the epicardium;
        whereby the epicardium is stabilized by the platform being temporarily attached to the epicardium; and
        whereby a section of an artery is occluded by positioning the at least one occluding member into engagement with the artery or epicardium above the artery, thereby temporarily occluding the artery.

2. The assembly of claim 1, wherein the platform includes a plurality of grooves for receiving suture threads for temporarily attaching the platform to the epicardium using the suture threads.

3. The assembly of claim 2, wherein the suture threads extend into the epicardium and attach to the platform thereby tensioning an operational field defined by the platform.

4. The assembly of claim 1, wherein the platform has a substantially U-shaped configuration for defining an operational field.

5. The assembly of claim 1, wherein the platform is formed of a rigid biocompatible material taken from the group of materials including metal alloys, stainless steel, and rigid polymers.

6. The assembly of claim 1, wherein the platform is formed from a flexible biocompatible material.

7. The assembly of claim 6, wherein the flexible material includes a flexible polymer material.

8. The assembly of claim 1, wherein the platform includes a first leg and a second leg, the first and second legs being substantially parallel and spaced apart, and a connecting member attached to the first leg and the second leg.

9. The assembly of claim 8, wherein the connecting member further includes a length defining the distance between the first leg and the second leg.

10. The assembly of claim 9, wherein the connecting member length is adjustable so that the distance between the first leg and the second leg can be adjusted.

11. The assembly of claim 8, wherein the connecting member is flexible so that the first and second legs can pivot toward or away from each other and can pivot in multiple planes.

12. The assembly of claim 8, wherein the first leg includes a first slot for receiving a first occluding member, the first occluding member configured for removable locking engagement with the first slot.

13. The assembly of claim 8, wherein the second leg includes a second slot for receiving a second occluding member, the second occluding member configured for removable locking engagement with the second slot.

14. The assembly of claim 13, wherein the first and the second occluding members include a first end for contacting the artery or the epicardium above the artery, a second end configured for grasping with forceps or fingers, and an elongated body extending between the first and the second ends.

15. The assembly of claim 14, wherein-the first and the second occluding members include a rigid elongate core and a body portion covering at least a portion of the rigid elongate core.

16. The assembly of claim 8, wherein the connecting member is malleable so that the first leg and the second leg can be moved in any direction and can be twisted to conform to the contour of the epicardium of the heart.

17. The assembly of claim 1, wherein the platform includes a plurality of hooks for engagement with the epicardium to temporarily attach the platform to the epicardium.

18. The assembly of claim 1, wherein at least a portion of the bottom surface of the platform includes a concave portion so that when the platform is pressed onto the epicardium it does not occlude an artery.

19. The assembly of claim 18, wherein the first and the second legs each have a top surface and a bottom surface, at least a portion of the bottom surface includes the concave portion so that when the legs are positioned over an artery the concave portion does not occlude the artery.

20. The assembly of claim 1, wherein means are provided for attaching the platform to the epicardium so that the epicardium can be tensioned and stabilized within the platform.

21. An assembly for stabilizing the epicardium of the heart and occluding a section of an artery, comprising:
    a platform having a top surface and a bottom surface, at least a portion of the bottom surface configured for contacting the epicardium of the heart;

at least one occluding member configured for adjustable movement relative to the platform; and an adjustable arm having a first end for removable attachment to the top surface of the platform longitudinal axis of the and a second end for removable attachment to a support that is stationary relative to the platform, the adjustable arm having a first flexible configuration for adjusting the distance between the platform and the support, and a second rigid configuration for fixing the platform relative to the support;

whereby the epicardium is stabilized by applying compressive force to the platform, the distance between the platform and the support defined by the adjustable arm to increase or decrease the compressive force on the epicardium by adjusting the distance between the platform and the support; and whereby a section of an artery can be occluded by positioning at least one occluding member into engagement with the artery or the epicardium above the artery, thereby temporarily occluding the artery.

22. The assembly of claim 21, wherein the platform includes a first slot and a second slot, and wherein a first occluding member and a second occluding member are retained respectively in the first slot and the second slot.

23. The assembly of claim 22, wherein the first and the second occluding members are configured for slidable and vertical movement in the first and the second slots respectively, and upon twisting the members, for releasable locking engagement in the first slot and the second slot respectively.

24. The assembly of claim 22, wherein the platform includes a first leg and a second leg, the first and second legs being substantially parallel and spaced apart, and a connecting member attached to the first leg and the second leg.

25. The assembly of claim 24, wherein the connecting member further includes a length defining the distance between the first leg and the second leg.

26. The assembly of claim 25, wherein the connecting member length is adjustable so that the distance between the first leg and the second leg can be adjusted.

27. The assembly of claim 24, wherein the connecting member is flexible so that the first and second legs can pivot toward or away from each other and can pivot in multiple planes.

28. The assembly of claim 24, wherein the first leg includes the first slot for receiving the first occluding member.

29. The assembly of claim 24, wherein the second leg includes the second slot for receiving the second occluding member.

30. The assembly of claim 24, wherein the connecting member is malleable so that the first leg and the second leg can be moved in any direction and can be twisted to conform to the contour of the epicardium of the heart.

31. The assembly of claim 24, wherein the first and the second legs each have a top surface and a bottom surface, at least a portion of the bottom surface having a concave portion so that when the legs are positioned over an artery the concave portion does not occlude the artery.

32. The assembly of claim 21, wherein the platform includes a plurality of grooves for receiving suture threads for attaching the platform to the epicardium.

33. The assembly of claim 32, wherein the suture threads extend into the epicardium and attach to the platform thereby tensioning an operational field defined by the platform.

34. The assembly of claim 21, wherein the platform has a substantially U-shaped configuration for defining an operational field.

35. The assembly of claim 21, wherein the platform is formed of a rigid biocompatible material taken from the group of materials including metallics, stainless steel, and rigid polymers.

36. The assembly of claim 21, wherein at least a portion of the platform is formed from a flexible biocompatible material.

37. The assembly of claim 36, wherein the flexible material includes a flexible polymer material.

38. The assembly of claim 21, wherein the first and the second occluding members include a first end for contacting the artery, a second end configured for grasping with forceps or fingers, and an elongated core extending between the first and the second ends.

39. The assembly of claim 38, wherein the first and the second occluding members include a rigid elongate core and a body portion covering at least a portion of the rigid elongate core.

40. The assembly of claim 39, wherein the first end of the resilient body is configured to provide atraumatic contact to occlude the artery.

41. The assembly of claim 21, wherein the adjustable arm includes a locking mechanism allowing the arm to be flexible when the mechanism is in an unlocked position, and rigid when the mechanism is in a locked position.

42. The assembly of claim 21, wherein at least a portion of the bottom surface of the platform includes a concave portion so that when the platform is pressed onto the epicardium it does not occlude an artery.

43. The assembly of claim 21, wherein a clamp is associated with the second end of the adjustable arm, the clamp being configured for removable attachment to the stationary support.

44. The assembly of claim 21, wherein means are provided for attaching the platform to the epicardium so that the epicardium can be tensioned and stabilized within the platform.

45. An assembly for stabilizing the epicardium of the heart and occluding a section of an artery, comprising:

a platform having a top surface and a bottom surface, at least a portion of the bottom surface configured for contacting the epicardium of the heart;

a first slot and a second slot disposed in the platform;

a first occluding member and a second occluding member retained respectively in the first slot and the second slot, the first and the second occluding members configured for adjustable movement relative to the platform; and an adjustable arm having a first end for removable attachment to the top surface of the platform and a second end for removable attachment to a support that is stationary relative to the platform, the adjustable arm having a first flexible configuration for adjusting the distance between the platform and the support, and a second rigid configuration for fixing the platform relative to the support;

whereby the epicardium is stabilized by applying compressive force to the platform, the distance between the platform and the support defined by the adjustable arm which will increase or decrease the compressive force on the epicardium by adjusting the distance between the platform and the support; and whereby a section of an artery can be occluded by positioning the first and the second occluding members into engagement with the artery or the epicardium above the artery, thereby temporarily occluding the artery.

46. The assembly of claim 45, wherein the platform includes a plurality of grooves for receiving suture threads for attaching the platform to the epicardium.

47. The assembly of claim 49, wherein the first and the second legs each have a top surface and a bottom surface, at least a portion of the bottom surface being recessed so that when the legs are positioned over an artery the recessed portion does not occlude the artery.

48. The assembly of claim 46, wherein the suture threads extend into the epicardium and attach to the platform thereby tensioning an operational field defined by the platform.

49. The assembly of claim 45, wherein the platform includes a first leg and a second leg, the first and second legs being substantially parallel and spaced apart, and a connecting member attached to the first leg and the second leg.

50. The assembly of claim 49, wherein the connecting member further includes a length defining the distance between the first leg and the second leg.

51. The assembly of claim 50, wherein the connecting member length is adjustable so that the distance between the first leg and the second leg can be adjusted.

52. The assembly of claim 51, wherein the connecting member is flexible so that the first and second legs can pivot toward or away from each and can pivot in multiple planes.

53. The assembly of claim 49, wherein the first leg includes the first slot for receiving the first occluding member and the second leg includes the second slot for receiving the second occluding member.

54. The assembly of claim 49, wherein the connecting member is formed from a malleable material so that the first leg and the second leg can be moved in any direction and can be twisted to conform to the contour of the epicardium of the heart.

55. The assembly of claim 45, wherein the first and the second occluding members are configured for slidable movement in the first and the second slots respectively, and upon twisting the members, for releasable locking engagement in the first slot and the second slot respectively.

56. The assembly of claim 45, wherein a clamp is associated with the second end of the adjustable arm, the clamp being configured for removable attachment to the stationary support.

57. The assembly of claim 45, wherein at least a portion of the bottom surface of the platform is recessed so that when the platform is pressed onto the epicardium it does not occlude an artery.

58. The assembly of claim 45, wherein means are provided for attaching the platform to the epicardium so that the epicardium can be tensioned and stabilized within the platform.

59. A method for stabilizing the heart and occluding an artery, the method steps comprising:

provuding a platform having a top surface and a bottom surface, at least a portion of the bottom surface configured for contacting the epicardium of the heart, a first occluding member and a second occluding member configured for slidable and vertical movement within the platform;

positioning the platform on the epicardium;

positioning the first and the second occluding members over a section of artery;

temporarily occluding the section of artery with the occluding members;

performing a medical procedure;

releasing the occluding members and detaching the platform from the epicardium; and removing the tool from the patient.

60. The method of claim 59, wherein the platform is removably attached to the epicardium by suturing threads connected to the platform and to a portion of the epicardium.

61. The method of claim 59, wherein the step of providing a platform includes providing a platform having a substantially U-shape, a first leg and a second leg connected by a connector, and a first slot in the first leg and a second slot in the second leg for slidably receiving the first and second occluding members respectively.

62. The method of claim 61, wherein the step of positioning the occluding members includes sliding the first and the second occluding members in the first and the second slots respectively for positioning the occluders over the section of an artery.

63. The method of claim 62, wherein the first and the second occluding members are temporarily locked in the first and the second slots, the occluding members occluding the section of artery.

64. The method of claim 61, wherein the first leg is moveable relative to the second leg, the further method step including adjusting the first leg relative to the second leg to position the first occluding member and the second occluding member over a section of artery.

65. The method of claim 59, wherein the step of providing the platform further includes providing an adjustable arm having a first end for removable attachment to a top surface of the platform and a second end for removable attachment for a support that is stationary relative to the platform, the adjustable arm having a first flexible configuration for adjusting the distance between the platform and the support, and a second rigid configuration for fixing the platform relative to the stationary support.

66. The method of claim 65, wherein after the step of positioning the platform on the epicardium, the method steps for stabilizing the epicardium include:

clamping the adjustable arm to the stationary support;

adjusting the distance between the stationary support and the epicardium by pressing the platform on the epicardium and locking the adjustable arm in the second rigid configuration thereby fixing the platform relative to the support and the epicardium providing a stable surface on the epicardium.

67. The method of claim 66, wherein after the step of performing the medical procedure, the adjustable arm is unclamped from the stationary support and the platform is removed from the epicardium.

\* \* \* \* \*